United States Patent [19]
Higuerey et al.

[11] Patent Number: 5,939,650
[45] Date of Patent: Aug. 17, 1999

[54] METHOD FOR DETERMINING SUITABILITY OF FLUID

[75] Inventors: Evelitsa E. Higuerey, Middletown; Paul J. Doukas, Wallingford, both of Conn.

[73] Assignee: United Technologies Corporation, Hartford, Conn.

[21] Appl. No.: 09/146,466

[22] Filed: Sep. 3, 1998

[51] Int. Cl.[6] .............................. G01N 33/00; B23H 1/08
[52] U.S. Cl. .......................................... 73/866; 219/69.14
[58] Field of Search ..................... 73/866, 32 R; 340/603, 604, 605; 219/69.14, 69.19, 69.17; 702/50, 57, 137; 324/425, 432; 205/649, 650, 654

[56] References Cited

U.S. PATENT DOCUMENTS

| | | | |
|---|---|---|---|
| 4,392,110 | 7/1983 | El-Menshawy et al. | 324/453 |
| 4,409,458 | 10/1983 | Inoue | 219/69 D |
| 4,551,809 | 11/1985 | Marendaz | 364/474 |
| 4,885,066 | 12/1989 | Kuwabara et al. | 204/129.43 |
| 4,888,462 | 12/1989 | Kiot et al. | 219/69.2 |

*Primary Examiner*—Hezron Williams
*Assistant Examiner*—Helen C. Kwok
*Attorney, Agent, or Firm*—Mark Steinberg

[57] ABSTRACT

A method of inspection for a fluid to determine its suitability for use as a dielectric medium in an EDM system and a method of maintenance for an EDM system having a dielectric fluid include generating an indication of the density of a sample of the fluid, providing at least one reference associated with at least one measure of suitability of the fluid, and comparing the indication to the at least one reference to determine, in the case of the method of inspection, the suitability of the fluid for use in the system, and in the case of the method of maintenance, whether to replace the fluid in the EDM system.

16 Claims, 4 Drawing Sheets

FIG. 4
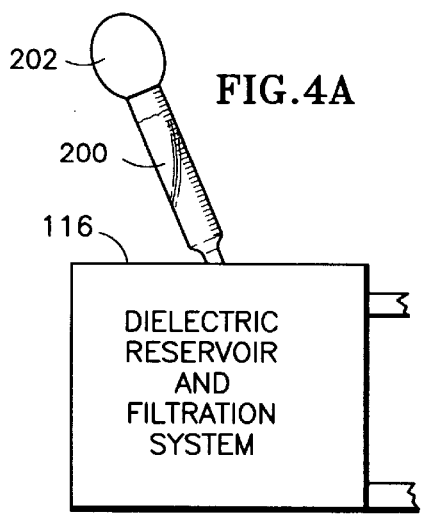
FIG. 4A
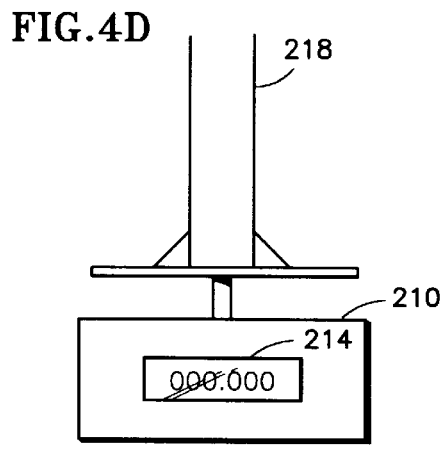
FIG. 4D
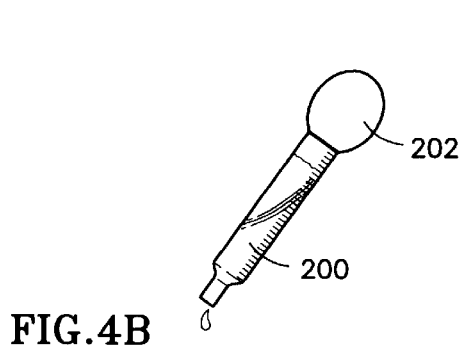
FIG. 4B
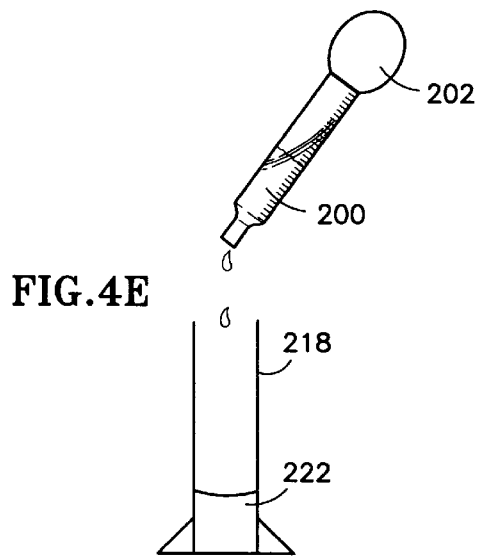
FIG. 4E
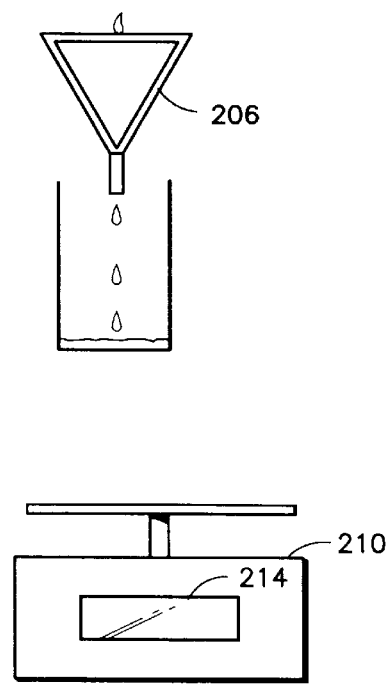
FIG. 4C
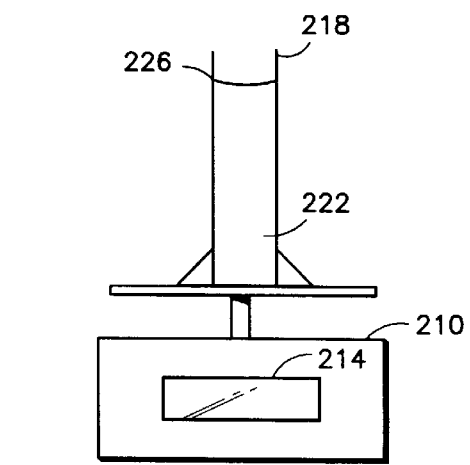
FIG. 4F

METHOD FOR DETERMINING SUITABILITY OF FLUID

DESCRIPTION

1. Technical Field

This invention relates to a method of inspecting a fluid to determine its suitability for a certain purpose, and more particularly to a method that determines the suitability of the fluid on the basis of the density of the fluid.

2. Background

Fluids are often used in machinery and in manufacturing processes. For example, in the art of electrical discharge machining ("EDM"), a dielectric liquid fluid fills a gap between an electrode and a work area on a workpiece. The fluid serves as a medium for transmitting high energy electrical discharges (i.e., pulses of high current) between the electrode and the work area. The discharges are generated by applying a differential voltage between the electrode and the workpiece, thereby inducing a dielectric breakdown, or high current, condition in the fluid. The discharges result in heat generation and melting at the work area. The fluid flushes molten material (i.e., debris) away from the work area and dissipates excess heat from the workpiece.

The quality of machining provided by an EDM process depends in large part on the suitability of the dielectric fluid. Generally speaking, any fluid may be characterized according to various qualities or properties, including but not limited to, specific gravity, density, weight, viscosity, dielectric strength, evaporation rate, flash point, boiling point, acidity, color and odor. Two important properties for a fluid used in EDM are dielectric strength and viscosity. The dielectric strength of the EDM fluid affects the amount of energy delivered to the workpiece. Too high or too low of a dielectric strength can result in delivery of too little or too much energy, respectively. The viscosity of the EDM fluid affects its ability to flush away debris and dissipate heat. A relatively low viscosity results in better flushing and more effective heat dissipation.

However, the suitability of the EDM fluid degrades over time with use. For example, repetitive breakdown of the EDM fluid causes a decrease in its dielectric strength. Furthermore, during breakdown, the relatively lighter, less viscous components in the dielectric fluid evaporate, causing the density and the viscosity of the fluid to increase. In addition, the dielectric fluid can become contaminated with other types of fluid, e.g., hydraulic fluid, employed within the EDM system. Such contamination often raises the viscosity of the dielectric fluid. The dielectric fluid can also become contaminated with debris from the EDM process. Debris can divert energy from the workpiece, thereby reducing the rate at which material is removed from the workpiece. This leads to incomplete or inaccurate machining. The debris can also effect a reduction in the dielectric strength of the dielectric fluid and/or result in arcing, which can damage the tools and the workpiece.

Therefore, it is important that the fluid be periodically inspected for its continued suitability for the EDM process. However, even though EDM systems have been used for decades, there has been a lack of a reasonably simple and reliable method for inspecting the EDM fluid for suitability. One known fluid inspection method involves measuring the viscosity and comparing it to a reference value. However, measuring viscosity typically entails a complex procedure that must be performed by trained personnel or complex instrumentation under tightly controlled environmental (e.g., temperature) conditions to obtain accurate results.

Another method of determining the EDM fluid suitability involves the use of magnetic and/or capacitance measurements to detect the presence of debris, or particles, in the fluid. However, this method requires complex and expensive instrumentation, and provides information relating to the amount of contamination, but does not provide information regarding the suitability of the fluid itself. Other methods are acidity and clarity testing, but as with contamination testing, these methods typically do not provide sufficient information. Commercial laboratories can measure many fluid properties to assess its suitability. However, the use of a commercial laboratory is often costly and may preclude a speedy determination if the laboratory is remotely located.

SUMMARY OF THE INVENTION

An object of the present invention is to provide a reasonably simple and reliable method of inspecting a fluid to determine the suitability of the fluid.

Another object of the present invention is to provide a method of inspecting a fluid to determine its suitability within a reasonably short duration and available environmental conditions.

The present invention is predicated on the fact that there is a correlation between fluid density and suitability of the fluid for use as a dielectric medium in an EDM process. Fluid suppliers traditionally specify a density for their fluids; however, they do not disclose or suggest measuring the fluid density to determine the suitability of the fluid.

According to a first aspect of the present invention, a method of inspecting a fluid to determine its suitability for use as a dielectric medium in an EDM system includes generating an indication of the density of a sample of the fluid, providing at least one reference associated with at least one measure of suitability of the fluid, and comparing the indication to the at least one reference.

According to a second aspect of the present invention, a method of maintenance for an EDM system having a fluid includes generating an indication of the density of a sample of the fluid, providing at least one reference associated with at least one measure of suitability of the fluid, comparing the indication to the reference, and determining, on the basis thereof, whether to replace the fluid.

The present invention provides a method that compares an indication of fluid density to a reference associated with a measure of suitability of the fluid, thereby enabling reasonably simple, reliable, and quick testing of a fluid to determine its suitability, under reasonably available environmental conditions. The reference is preferably determined using empirical methods, although analytical methods and combinations thereof, may also be used. In a preferred embodiment, the density of the fluid is determined quickly and accurately by EDM personnel in an EDM shop area using off the shelf equipment.

These and other objects, features and advantages of the present invention will become more apparent in the light of the following detailed description, accompanying drawings, and claims.

BRIEF DESCRIPTION OF THE DRAWINGS

FIG. 4, including FIGS. 4A–4F, is a plurality of illustrations depicting equipment of the fluid inspection system of FIG. 1 as used to carry out the steps of the flowchart of FIG. 3.

BEST MODE FOR CARRYING OUT THE INVENTION

Figure 1:
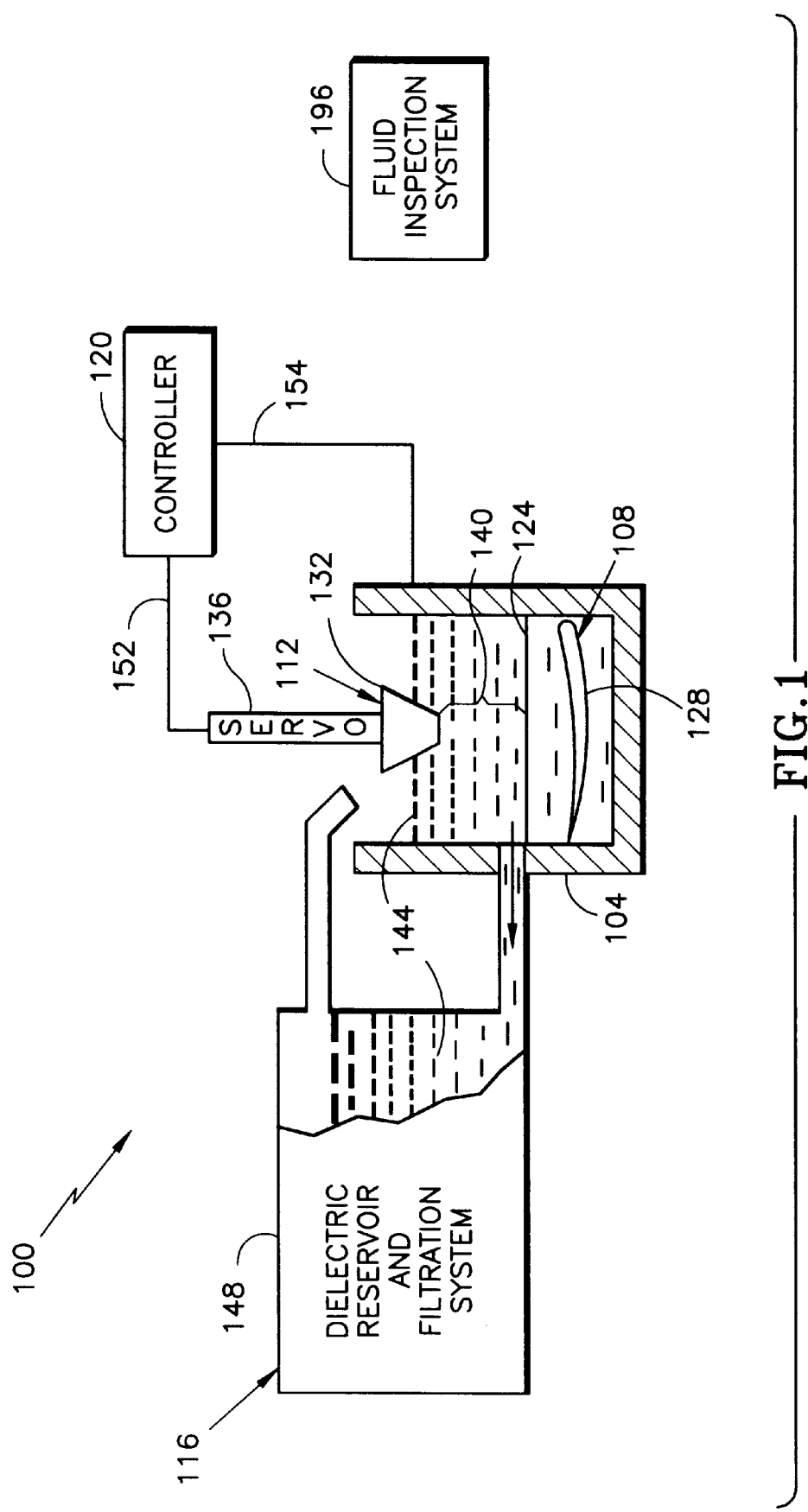
FIG. 1 is a representation of an EDM system for drilling holes in turbine airfoils, in combination with a representation of a fluid inspection system for carrying out the inspection method of the present invention.

The present invention is disclosed herein with respect to a best mode embodiment for use in inspecting fluid from a well known EDM system used to drill cooling holes in turbine blades, as represented in FIG. 1. Referring now to FIG. 1, the EDM system 100 has a fixture 104 for positioning a turbine blade 108 (i.e., a workpiece), an electrode subsystem 112, a dielectric subsystem 116, and a controller 120. The turbine blade 108 may have a platform 124 and an airfoil 128. The electrode subsystem 112 includes an electrode 132 and a servo mechanism 136 that moves the electrode 132 toward or away from the turbine blade 108 to narrow or widen a gap 140 between the electrode 132 and a work area on the workpiece. The dielectric subsystem 116 includes a dielectric fluid 144, e.g., model EDM-244™ commercially available from Commonwealth Oil, and a dielectric reservoir/filtration system 148. The dielectric fluid 144 fills the gap 140 between the electrode 132 and the work area on the workpiece 108. The controller 120 is electrically connected to the fixture 104 and the electrode subsystem 112 by signal lines 152, 154.

In the operation of the EDM system 100, the controller 120 causes a differential voltage to be applied between the electrode 132 and the workpiece 108. The applied voltage causes a breakdown condition in the dielectric fluid 144, whereby a high current flows between the electrode 132 and the workpiece 108. The high current causes melting in the work area of the workpiece 108, thereby removing desired portions of the workpiece 108. The dielectric fluid 144 flushes away the molten material removed from the workpiece 108.

As described above, it is well known that the suitability of the EDM fluid 144 degrades over time with use, yet it has traditionally been difficult to determine when the fluid 144 is no longer suitable for use. The extent of degradation could be determined by measuring fluid viscosity and/or dielectric strength, but oftentimes, there is no convenient way to make such measurements.

Figure 2:
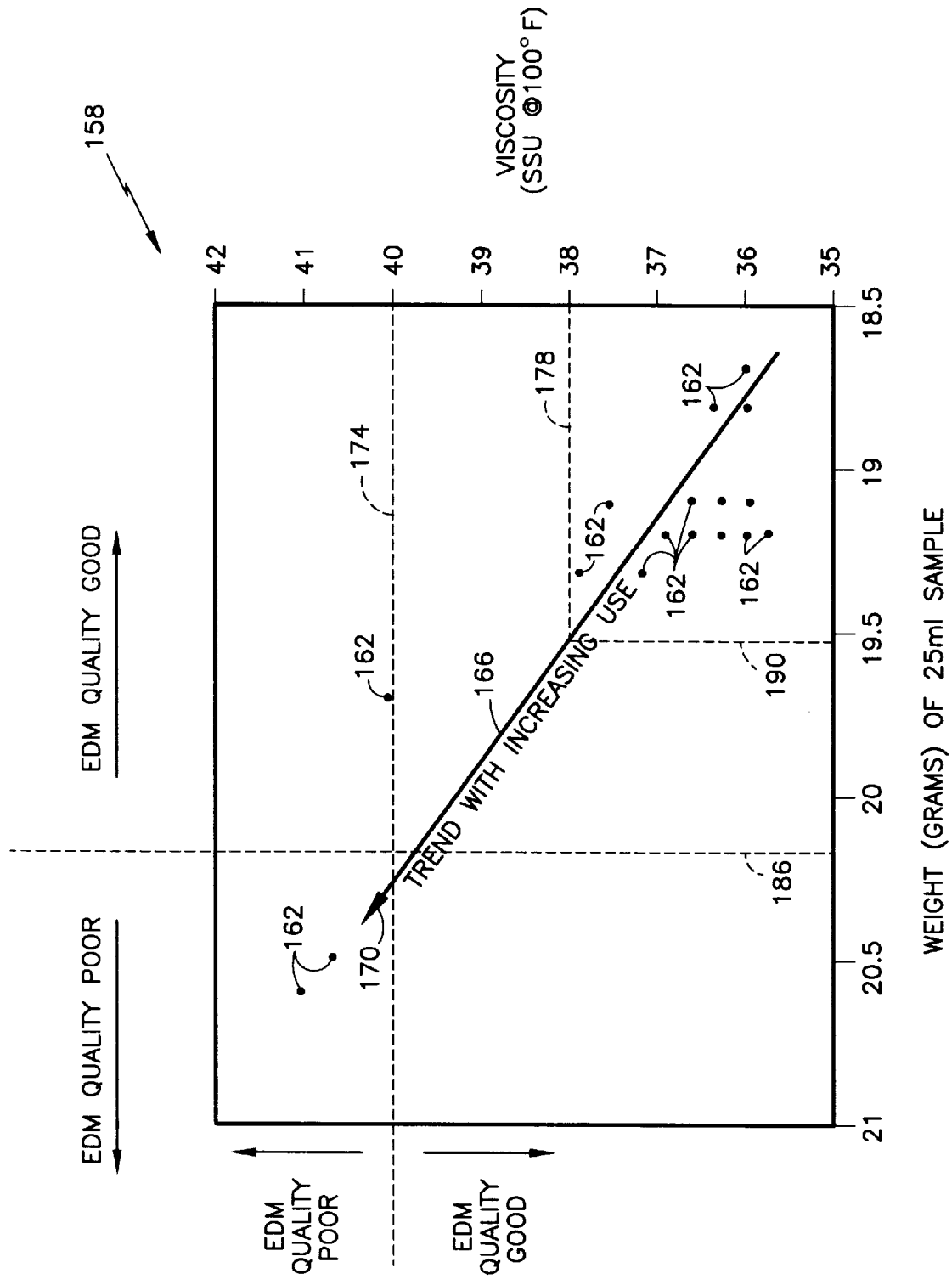
FIG. 2 is a graph of data points indicative of viscosity and density measurements for various fluids, after varying amounts of usage of the fluids in the EDM system of FIG. 1.

However, it has now been determined that there is a correlation between the suitability of the fluid 144 and the fluid density. Referring also now to FIG. 2, a chart 158 has a plurality of data points 162 indicative of viscosity and density characteristics of various EDM fluids after varying amounts of use. Each individual data point 162 is indicative of the viscosity of one of the various EDM fluids after having undergone one of the various amounts of usage, and is also indicative of the density of the fluid 144 after the usage. The density of the fluid 144 is preferably determined by weighing a known volume of the fluid 144 and dividing the magnitude of the weight by the magnitude of the volume. A solid line 166 represents a least squares fit linear approximation for the data. This line is not to imply a strong correlation between fluid density and fluid viscosity, but rather to represent a limited correspondence between viscosity and density over the limited ranges of density and viscosity that appear on the chart 158. An arrowhead 170 on the line 166 indicates a general trend of the viscosity and the density with increasing use, all else being equal. This trend suggests a correlation between fluid density and fluid suitability over varying types of fluid 144 and amounts of usage.

Reference fluid densities indicative of fluid suitability may be determined by referring to fluid viscosities known to result in satisfactory EDM quality. For example, a first horizontal dotted line 174 indicates the maximum fluid viscosity with which the EDM system 100 provides satisfactory quality results, i.e. viscosities above the first dotted line result in unsatisfactory EDM quality. A second horizontal dotted line 178 specifies a maximum allowed fluid viscosity for the fluid 144 used in the EDM system 100. An intersection of the first horizontal line 174 and the solid line 166 is indicative of a maximum fluid density, indicated by a first vertical dotted line 186, with which the EDM system 100 provides satisfactory results. An intersection of the second horizontal line 178 and the solid line 166 establishes a maximum allowed fluid density, indicated by a second vertical dotted line 190, for the fluid 144 in the EDM system 100. However, these densities are by no means the only densities suitable for use in the EDM system 100. Furthermore, different EDM processes may warrant different fluid densities. Of course, suitable fluid densities may alternatively be determined directly, without reference to a fluid viscosity.

Figure 3:
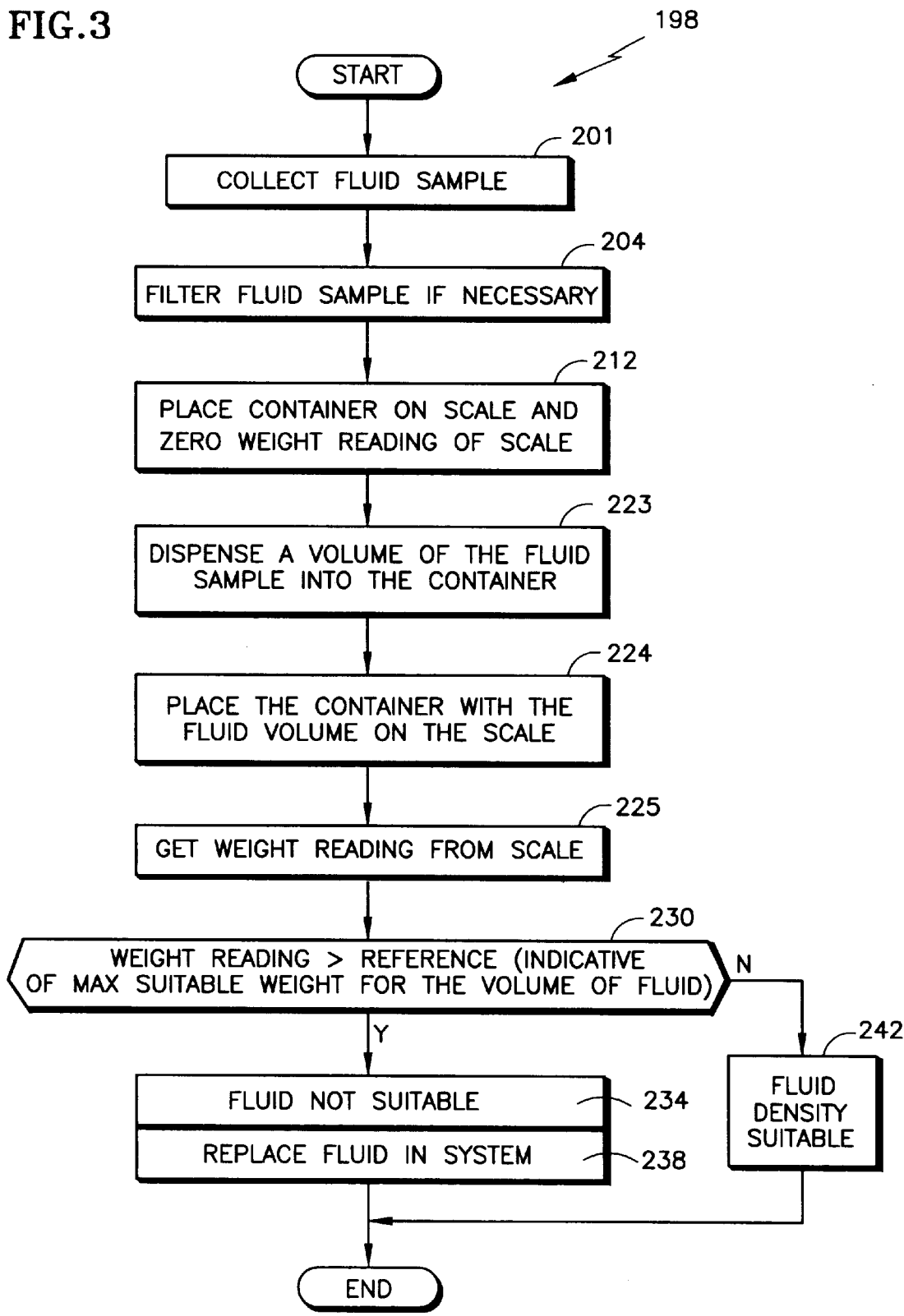
FIG. 3 is a flowchart of steps in a best mode embodiment of the inspection method of the present invention, carried out by the fluid inspection system of FIG. 1.

In the best mode embodiment, the fluid inspection method of the present invention is carried out by a fluid inspection system 196. Referring now to FIGS. 3 and 4, a flowchart 198 (FIG. 3) lists a plurality of steps carried out by the fluid inspection system 196 (FIG. 1), and a plurality of illustrations (FIG. 4, including FIGS. 4A–4F) depict equipment of the fluid inspection system 196 as used to carry out the steps of the flowchart 198. Initially, a sample 200 of the fluid 144 in the EDM system 100 is first collected in a step 201 using, for example, a graduated, calibrated pipette 202 (FIG. 4A). In a step 204, the sample 200 (FIG. 4B) may be passed through a filter 206, e.g., number 2 Whatman filter paper having medium porosity to remove debris, although such filtering is not necessary. A scale 210 (FIG. 4C) is provided, and in a step 212, a container 218 (FIG. 4D) is placed on the scale 210 and the weight reading of the scale is zeroed. A volume 222 (FIG. 4E), e.g. 25 milliliters ("ml"), of the fluid sample 200 is then dispensed in a step 223 into the container 218. In a step 224, the container 218 is placed on the scale 210 (FIG. 4F) to get a reading 214 indicative of the weight of the fluid volume 222. Taken together, the weight and the size 226 of the volume 222 provide an indication of the density of the fluid 144.

The magnitude of the weight is compared in a step 230 to a reference magnitude, indicative of a maximum suitable weight for the fluid volume 222. In the best mode embodiment, the reference magnitude is preferably chosen to correspond with the density indicated by the second vertical dotted line 190 (FIG. 2). If the weight exceeds the reference magnitude, then a determination is made in a step 234 that the fluid 144 is unsuitable for continued use and is replaced in the EDM system 100 in a step 238. In such case it may be desirable to inspect the color of the fluid 144 to determine whether contamination by hydraulic fluid contributed to the unsuitability. Uncontaminated dielectric fluid 144 is typically clear, while hydraulic fluid is commonly brownish. If the weight does not exceed the reference magnitude, then a determination is made in a step 242 that the fluid 144 has a suitable density. As such, the EDM fluid 144 may be determined to be suitable for continued use in the EDM process. However, overall suitability may depend on additional criteria, for example, the amount of debris in the fluid 144.

The present invention represents a significant improvement over traditional fluid inspection methods. In particular, the best mode embodiment provides a method for EDM personnel to determine the suitability of the fluid reasonably quickly and accurately using off the shelf equipment in an EDM shop area. The area may have substantially no temperature control. This is because, in the best mode embodiment, the temperature or the equipment in the inspection system and the temperature of the fluid sample need not be controlled. However, the inspection system could incorporate mechanisms to control the temperature of the inspection system equipment and/or the fluid sample, if desired. As used herein, substantially no temperature control means that the temperature of the ambient air can fluctuate significantly, e.g., +/−5 degrees Fahrenheit (F.), although some areas having substantially no temperature control could experience temperature fluctuations of +/−10 degrees F., +/−25 degrees F., or even more. As the magnitude of temperature fluctuations increases, it becomes increasingly difficult to obtain consistency in certain types of measurements, e.g., viscosity measurements.

While the present invention has been described with reference to a best mode embodiment, this description is not meant to be construed in a limiting sense. Various modifications of the best mode of embodiment, as well as additional embodiments of the invention, will be apparent to persons skilled in the art upon reference to this description, without departing from the spirit of the invention, as recited in the claims appended hereto. For example, any indication of fluid density may be used to determine the suitability of the fluid. Thus, even though the best mode embodiment uses the weight of a volume of the fluid, other indications may be used including, but not limited to, the actual density of the fluid, the specific gravity (i.e., relative density) of the fluid, the relative weight of a volume of the fluid, the buoyant forces of the fluid, and /or the sheer stresses of the fluid. Specific gravity may be determined using a hydrometer. Weight may be determined with or without a scale, of which there are many different types including balance types. Buoyant forces could be determined, for example, by placing balls of appropriate weights into the fluid sample and observing which balls float. The steps and the equipment used to generate any particular indication of fluid density are a matter of choice. The methods used to determine a reference indicative of suitability are also a matter of choice. Although empirical methods are preferred for such, other methods for example analytical methods, and combinations thereof may also be used. References indicating suitability may be determined with or without reference to a viscosity range. The chart of FIG. 2 is merely a tool to explain the present invention and is not meant to imply that fluid viscosity data is needed to practice the method of the present invention. Any suitable size fluid sample may be used. Furthermore, the present invention may be used to determine the suitability of any fluid. Of course, the range of fluid densities suitable for one process may differ from that suitable for another process. It is therefore contemplated that the appended claims will cover any such modifications or embodiments as fall within the true scope of the invention.

All the foregoing variations are irrelevant to the broadest scope of the invention. It suffices for the broadest scope that a method includes generating an indication of the density of a sample of the fluid, providing at least one reference associated with at least one measure of suitability, and comparing the indication to the at least one reference.

What is claimed is:

1. A method of inspecting a fluid to determine its suitability for use as a dielectric medium in an EDM system, the method comprising the steps of:

generating an indication of a density of a sample of the fluid;

providing at least one reference indicative of at least one density associated with at least one measure of the suitability of the fluid;

comparing the indication to the at least one reference; and determining, on the basis of the comparison, the suitability of the fluid.

2. The method of claim 1, wherein the step of generating an indication of the density is carried out in an area having substantially no temperature control of ambient air.

3. The method of claim 1, wherein the step of generating an indication of the density is carried out in an EDM shop area.

4. The method of claim 1, wherein the step of generating an indication of the density is performed by an EDM operator.

5. The method of claim 1, wherein the step of generating an indication of the density is carried out without controlling a temperature of the sample of the fluid.

6. The method of claim 1, wherein the step of generating an indication of the density comprises generating an indication of a weight of a volume of the sample of the fluid.

7. The method of claim 6, wherein the step of generating an indication of the weight comprises weighing the volume of the sample of the fluid using a scale.

8. The method of claim 1, wherein the step of providing at least one reference comprises providing a reference weight indicative of a suitable density of the sample of the fluid.

9. A method of maintenance for an EDM system having a fluid used as a dielectric medium, the method comprising the steps of:

generating an indication of a density of a sample of the fluid;

providing at least one reference indicative of at least one density associated with at least one measure of the suitability of the fluid;

comparing the indication of the density to the at least one reference; and determining, on the basis of the comparison, whether to replace the fluid.

10. The method of claim 9, wherein the step of generating an indication of the density is carried out in an area having substantially no temperature control of ambient air.

11. The method of claim 9, wherein the step of generating an indication of the density is carried out in an EDM shop area.

12. The method of claim 9, wherein the step of generating an indication of the density is performed by an EDM operator.

13. The method of claim 9, wherein the step of generating an indication of the density is carried out without controlling a temperature of the sample of the fluid.

14. The method of claim 9, wherein the step of generating an indication of the density comprises generating an indication of a weight of a volume of the sample of the fluid.

15. The method of claim 14, wherein the step of generating an indication of the weight comprises weighing the volume of the sample of the fluid.

16. The method of claim 9, wherein the step of providing at least one reference comprises providing a reference weight indicative of a suitable density of the sample of the fluid.

* * * * *